US 9,921,188 B2

United States Patent
Takamine et al.

(10) Patent No.: US 9,921,188 B2
(45) Date of Patent: Mar. 20, 2018

(54) DETECTION SYSTEM AND DETECTION METHOD

(71) Applicant: KABUSHIKI KAISHA TOSHIBA, Tokyo (JP)

(72) Inventors: Hidefumi Takamine, Tokyo (JP); Kazuo Watabe, Kanagawa (JP); Takahiro Omori, Kanagawa (JP); Takashi Usui, Saitama (JP); Junko Hirokawa, Tokyo (JP); Akihiro Kasahara, Chiba (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 196 days.

(21) Appl. No.: 14/841,955

(22) Filed: Sep. 1, 2015

(65) Prior Publication Data
US 2016/0084803 A1  Mar. 24, 2016

(30) Foreign Application Priority Data
Sep. 18, 2014 (JP) ................................. 2014-190537

(51) Int. Cl.
*G01N 29/14* (2006.01)
*E04C 3/26* (2006.01)
(Continued)

(52) U.S. Cl.
CPC ............. *G01N 29/14* (2013.01); *E04C 3/26* (2013.01); *G01M 5/0033* (2013.01);
(Continued)

(58) Field of Classification Search
CPC .... G01N 29/14; G01N 29/22; G01N 29/4417; G01N 33/383; G01M 5/0008; G01M 5/0066; G01M 5/0041
See application file for complete search history.

(56) References Cited

U.S. PATENT DOCUMENTS

| 6,208,247 B1 * | 3/2001 | Agre ..................... G01V 1/223 340/13.25 |
| 6,399,939 B1 * | 6/2002 | Sundaresan .............. G01H 1/12 250/231.1 |

(Continued)

FOREIGN PATENT DOCUMENTS

| CN | 103702444 | 4/2014 |
| JP | 2003-315317 | 11/2003 |

(Continued)

OTHER PUBLICATIONS

Extended Eurpoean Search Report dated Feb. 23, 2016, directed to counterpart EP Application No. 15182973.6; 11 pages.

(Continued)

*Primary Examiner* — Helen Kwok
(74) *Attorney, Agent, or Firm* — Finnegan, Henderson, Farabow, Garrett & Dunner, L.L.P.

(57) ABSTRACT

According to an embodiment, a detection system includes a plurality of sensor nodes and a sensor module. The plurality of sensor nodes detects sound waves generated from a prestressed concrete and converts the detected sound waves into detection signals. The sensor module is connected to the plurality of sensor nodes and receives the detection signals. The plurality of sensor nodes includes the sensor nodes in an operating state and the sensor nodes in a dormant state in which power consumption is held down as compared to the operating state. When magnitude of the detection signals is equal to or greater than a first threshold value, the sensor module switches the sensor node in the dormant state to the operating state.

12 Claims, 10 Drawing Sheets

(51) Int. Cl.
*G01M 5/00* (2006.01)
*G01N 29/22* (2006.01)
*G01N 29/44* (2006.01)
*G01N 33/38* (2006.01)

(52) U.S. Cl.
CPC ......... *G01N 29/22* (2013.01); *G01N 29/4427* (2013.01); *G01N 33/383* (2013.01); *G01N 2291/0232* (2013.01); *G01N 2291/106* (2013.01); *H04Q 2209/823* (2013.01); *H04Q 2209/883* (2013.01)

(56) References Cited

U.S. PATENT DOCUMENTS

| | | | | |
|---|---|---|---|---|
| 8,138,968 | B1* | 3/2012 | Butler | G01S 7/003 342/118 |
| 8,400,162 | B1* | 3/2013 | Jannson | G01R 31/3651 320/132 |
| 8,885,559 | B2* | 11/2014 | Schmidt | G01D 21/00 340/539.13 |
| 2004/0066313 | A1 | 4/2004 | Ong et al. | |
| 2005/0017873 | A1* | 1/2005 | Liu | G01M 5/0008 340/870.01 |
| 2005/0080520 | A1* | 4/2005 | Kline | B03B 9/06 701/1 |
| 2008/0278319 | A1 | 11/2008 | Meiksin et al. | |
| 2010/0211359 | A1* | 8/2010 | Mehta | H04W 52/28 702/188 |
| 2010/0271199 | A1* | 10/2010 | Belov | G01M 5/00 340/539.3 |
| 2014/0254315 | A1* | 9/2014 | Rigsby | G01V 1/3808 367/15 |
| 2015/0179044 | A1* | 6/2015 | Wu | G08B 21/20 370/311 |
| 2015/0269830 | A1* | 9/2015 | Beldon | G08B 5/36 340/666 |
| 2016/0048135 | A1* | 2/2016 | Hill | A01G 25/167 405/37 |

FOREIGN PATENT DOCUMENTS

| | | |
|---|---|---|
| JP | 2004-061432 | 2/2004 |
| JP | 2006-163659 | 6/2006 |
| JP | 2012-251391 | 12/2012 |
| JP | 2013-8275 | 1/2013 |
| JP | 2014-36273 | 2/2014 |
| WO | WO-2004/112411 | 12/2004 |

OTHER PUBLICATIONS

Tomoki Shiotani et al., "Temporal and spatial evaluation of grout failure process with PC cable breakage by means of acoustic emission", *Construction and Building Materials* 48 (2013) 1286-1292.

\* cited by examiner

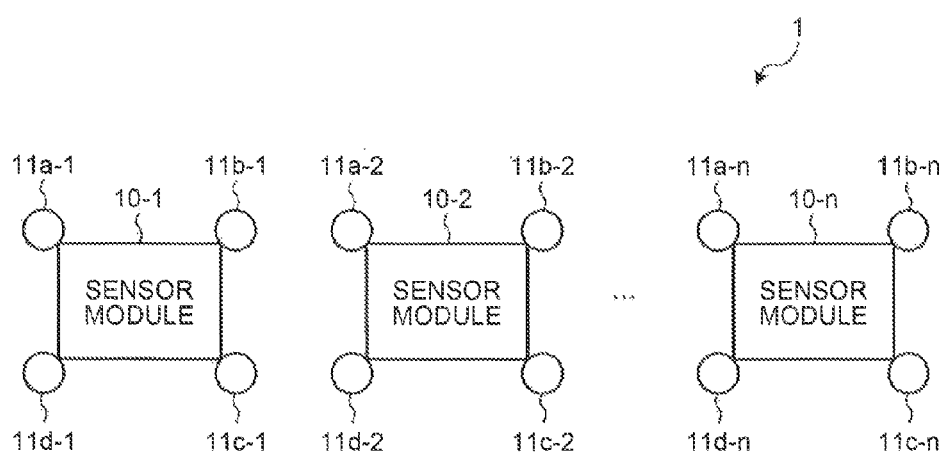

DETECTION SYSTEM AND DETECTION METHOD

CROSS-REFERENCE TO RELATED APPLICATIONS

This application is based upon and claims the benefit of priority from Japanese Patent Application No. 2014-190537, filed on Sep. 18, 2014; the entire contents of which are incorporated herein by reference.

FIELD

An embodiment described herein relates generally to a detection system and a detection method.

BACKGROUND

In prestressed concrete, if there remains void in the grouting inside a sheath due to defective construction work, then there are times when a fracture develops in a prestressed concrete (PC) cable at the position of the void. The sound generated when a fracture develops in the PC cable can be detected using an acoustic emission (AE) sensor. Moreover, for a short while after the fracture has developed, the frictional sound attributed to sliding and refitting of the cable and grout can also be detected using the AE sensor.

The phenomenon of developing a fracture in the PC cable inside the prestressed concrete happens in a flash and in an unexpected manner. However, in the conventional technology, after the PC cable refits in a stable state, there is no detection of any abnormality indicating that the prestressed concrete has become weaker in strength. For that reason, the AE sensor needs to be kept operational on a constant basis.

BRIEF DESCRIPTION OF THE DRAWINGS

FIG. 3 is a diagram illustrating an exemplary configuration of a detection system according to an embodiment;

FIG. 4 is a diagram illustrating an example of power supply states according to the embodiment;

DETAILED DESCRIPTION

According to an embodiment, a detection system includes a plurality of sensor nodes and a sensor module. The plurality of sensor nodes detects sound waves generated from a prestressed concrete and converts the detected sound waves into detection signals. The sensor module is connected to the plurality of sensor nodes and receives the detection signals. The plurality of sensor nodes includes the sensor nodes in an operating state and the sensor nodes in a dormant state in which power consumption is held down as compared to the operating state. When magnitude of the detection signals is equal to or greater than a first threshold value, the sensor module switches the sensor node in the dormant state to the operating state.

An exemplary embodiment of a detection system and a detection method is described below in detail with reference to the accompanying drawings.

Firstly, the explanation is given about the characteristics of prestressed concrete.

Figure 1:
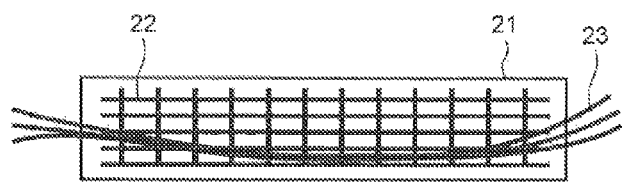
FIG. 1 is an explanatory diagram of prestressed concrete manufactured according to the post-tensioning method.

FIG. 1 is an explanatory diagram of prestressed concrete 21 manufactured according to the post-tensioning method. The prestressed concrete 21 includes, inside the concrete, reinforcing steel 22 and a sheath 23. Inside the sheath 23, a prestressed concrete (PC) cable is fixed by means of grouting. Because of the PC cable, a predetermined compression force gets applied to the prestressed concrete 21. That enables the prestressed concrete 21 to negate the stress attributed to being subjected to load. Hence, it can be ensured that no cracks are formed in the prestressed concrete 21.

Herein, if there remains void inside the sheath 23 due to insufficient grouting, then the PC cable becomes more prone to corrosion or fracture. If an acoustic emission (AE) sensor is installed on the outer surface of the prestressed concrete 21, it becomes possible to detect the sound waves generated when a fracture develops in the PC cable. More particularly, the AE sensor detects the sound waves generated from the prestressed concrete 21, and converts the detected sound waves into electrical signals. In the following explanation, such electrical signals are called AE signals (detection signals).

Moreover, if a plurality of AE sensors is installed on the outer surface of the prestressed concrete 21, it becomes possible to enhance the reliability of signal analysis. Moreover, from the differences in the arrival timings of the sound waves, the position of a fracture in the PC cable can be identified.

After a fracture develops in the PC cable, although the prestressed concrete 21 becomes weaker in strength, it settles down in a stable state. Hence, whether or not a fracture has developed is a difficult fact to measure afterwards using the AE sensor. Thus, in order to capture the moment at which a fracture develops in the PC cable, the AE sensor needs to be kept operational on a constant basis.

Meanwhile, regarding an infrastructure monitoring system, the requirement is to operate autonomously over long periods of time. Hence, it is important to hold down the power consumption. However, if the sensor is intermittently activated at regular intervals with the aim of achieving electrical power saving, then it is highly likely that the moment at which a fracture develops in the PC cable is missed.

In contrast, in the case of the prestressed concrete 21, after a fracture develops in the PC cable, when the PC cable refits in a stable state with the grout inside the sheath 23, a frictional sound is generated between the PC cable and the grout. That sound can be detected by the AE sensor.

Figure 2:
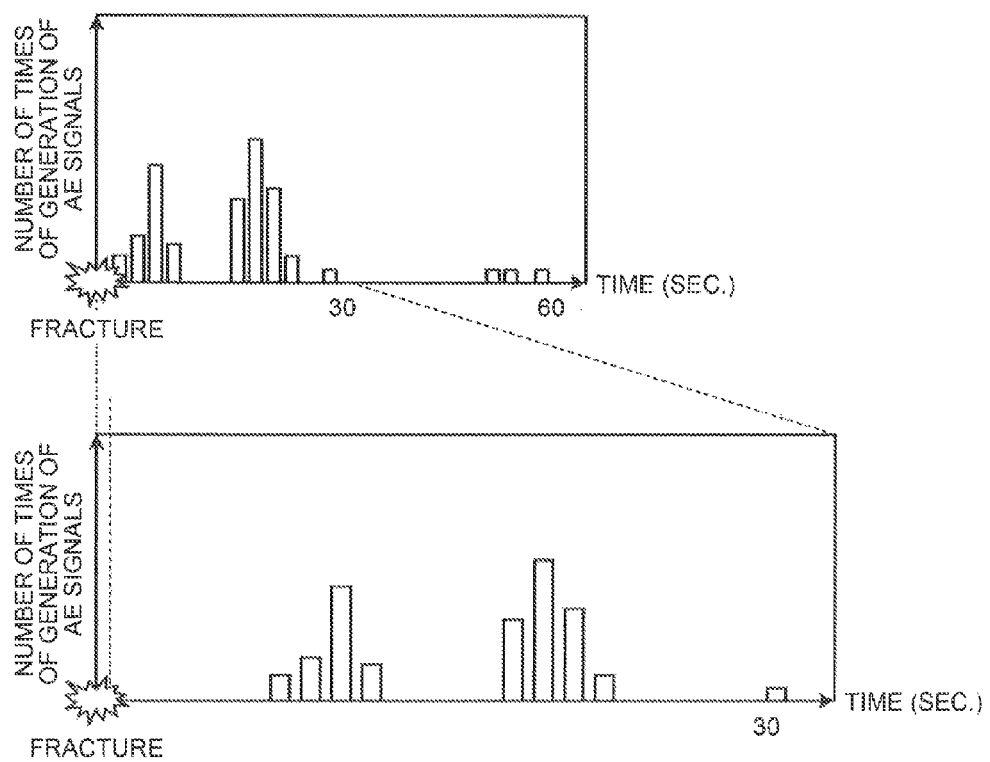
FIG. 2 is a diagram illustrating an example of the number of times of generation of acoustic emission (AE) signals when a fracture develops in a prestressed concrete (PC) cable.

FIG. 2 is a diagram illustrating an example of the number of times of generation of AE signals when a fracture develops in the PC cable. In the lower graph illustrated in FIG. 2, the graph area starting from the moment at which a fracture develops, which is illustrated in the upper graph in FIG. 2, till the elapse of 30 seconds is enlarged. As illustrated in FIG. 2, the AE sensor can detect the sound waves as AE signals during 30 seconds to one minute since the moment at which a fracture develops. By picking up the AE signals, the AE sensor can determine whether or not a fracture has developed.

Given below is the explanation of a detection system 1 according to the embodiment in which the phenomenon illustrated in FIG. 2 is used.

FIG. 3 is a diagram illustrating an exemplary configuration of the detection system 1 according to the embodiment. The detection system 1 includes a sensor module 10-1, sensor nodes 11a-1 to 11d-1, a sensor module 10-2, sensor nodes 11a-2 to 11d-2, . . . , a sensor module 10-n, and sensor nodes 11a-n to 11d-n.

In the following explanation, when the sensor modules 10-1, 10-2, . . . , and 10-n need not be distinguished from each other, they are simply referred to as sensor modules 10. In an identical manner, when the sensor nodes 11a-1 to 11d-1, the sensor nodes 11a-2 to 11d-2 . . . , and the sensor nodes 11a-n to 11d-n need not be distinguished from each other, they are simply referred to as sensor nodes 11.

Each sensor module 10 is a device that receives AE signals (detection signals) from the corresponding sensor nodes 11 and performs operations based on the AE signals. Each sensor node 11 detects the sound waves generated from the prestressed concrete 21 and converts the detected sound waves into AE signals. Herein, for example, each sensor node 11 is a piezoelectric element installed on the outer surface of the prestressed concrete 21.

Meanwhile, the number n of the sensor modules 10 can be an arbitrary number. Moreover, the number of sensor nodes 11 connected to each sensor module 10 is also not limited to four, and can be an arbitrary number. Furthermore, each sensor module 10 can have a different number of sensor nodes 11 connected thereto.

Given below is the explanation about the supply of electrical power to the detection system 1, the sensor module 10, and the sensor node 11.

FIG. 4 is a diagram illustrating an example of the power supply states according to the embodiment.

Firstly, the explanation is given about the power supply states of each sensor node 11. The power supply states of the sensor node 11 include an operating state and a dormant state. The operating state represents a power supply state in which the sensor node 11 is performing operations, that is, the state in which the sensor node 11 is measuring (detecting) the sound waves generated from the prestressed concrete 21. The dormant state represents a power supply state in which the sensor node 11 has stopped the operations, that is, the state in which the sensor node 11 does not measure (detect) the sound waves generated from the prestressed concrete 21. While being in the dormant state in which the power consumption is held down as compared to the operating state, the sensor node 11 waits for a return signal for returning to the operating state.

Given below is the explanation of the power supply states of each sensor module 10. The power supply states of the sensor module 10 include a first operating state, a second operating state, and a dormant state. The first operating state represents a power supply state in which, from among the sensor nodes 11 connected to the sensor module 10, some of the sensor nodes 11 are performing operations and the remaining sensor nodes 11 are not performing operations. The second operating state represents a power supply state in which all of the sensor nodes 11 connected to the sensor module 10 are performing operations. The dormant state represents a power supply state in which all of the sensor nodes 11 connected to the sensor module 10 have stopped the operations. Regarding the power supply states such as the first operating state, the second operating state, and the dormant state of each sensor module 10, the detailed explanation is given later.

Given below is the explanation of the power supply states of the detection system 1. The power supply states of the detection system 1 include a first operating state and a second operating state. The first operating state represents a power supply state in which some of the sensor modules 10 are in the first operating state and the remaining sensor modules 10 are in the dormant state, while some of the sensor nodes 11 are in the operating state and the remaining sensor nodes are in the dormant state. The second operating state represents a power supply state in which all of the sensor modules 10 are in the second operating state, while all of the sensor nodes 11 are in the operating state.

Herein, as long as the power consumption during the dormant state of the sensor modules 10 and the sensor nodes 11 is held down as compared to the power consumption during the operating states, the power consumption during the dormant state can be at an arbitrary level. For example, the power consumption during the dormant state can be zero too. Thus, in the explanation according to the embodiment, the dormant state includes the stopped state.

Given below is the explanation of an exemplary configuration of each sensor module 10 according to the embodiment.

Figure 5:
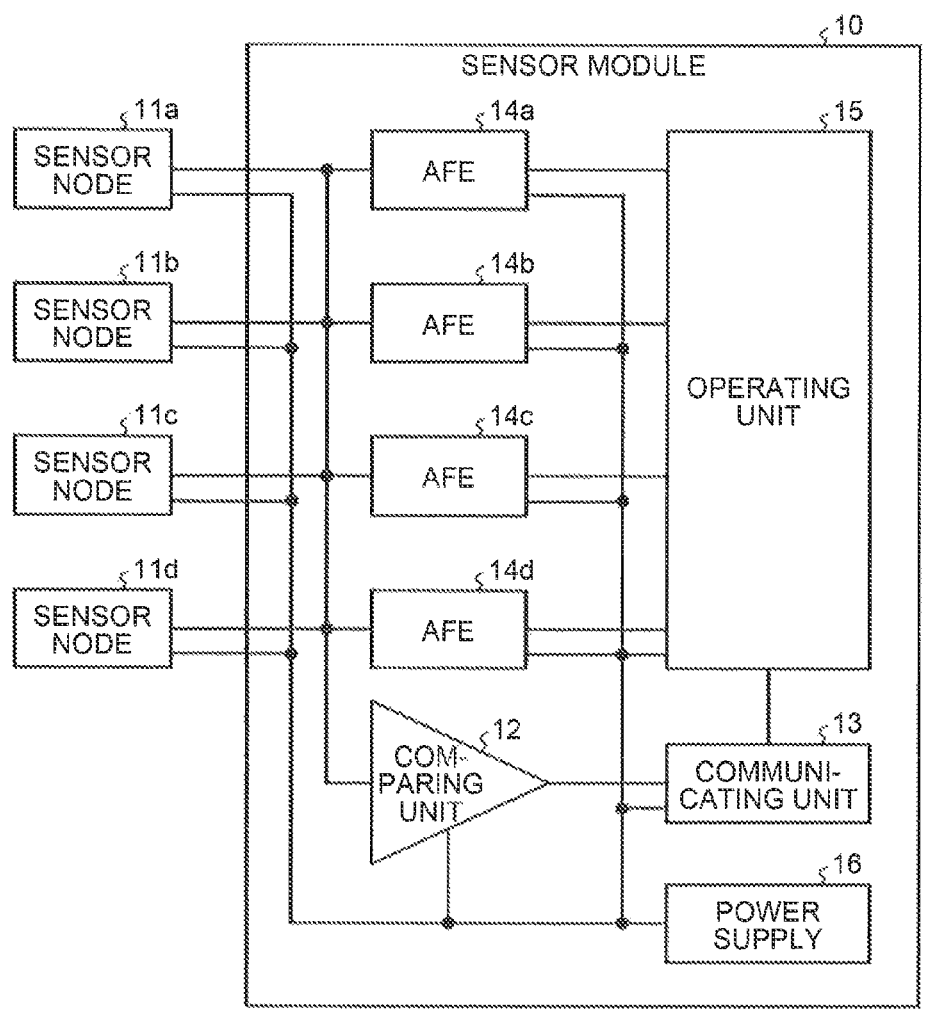
FIG. 5 is a diagram illustrating an exemplary configuration of a sensor module according to the embodiment.

FIG. 5 is a diagram illustrating an exemplary configuration of the sensor module 10 according to the embodiment. To the sensor module 10 are connected sensor nodes 11a to 11d. The sensor module 10 includes a comparing unit 12, a communicating unit 13, analog front ends (AFEs) 14a to 14d, an operating unit 15, and a power supply 16.

In the following explanation, when the AFEs 14a to 14d need not be distinguished from each other, they are simply referred to as AFEs 14.

The sensor node 11, the comparing unit 12, the AFEs 14, and the operating unit 15 operate either in the operating state or in the dormant state depending on the power supply state (the operating state, the second operating state, or the dormant state) of the sensor module 10.

Each sensor node 11 in the operating state detects the sound waves generated from the prestressed concrete 21 and converts the detected sound waves into AE signals (detection signals).

When the operating unit 15 is not performing operations (i.e., when the sensor module 10 is in the first operating state), the sensor nodes 11 in the operating state send AE signals to the comparing unit 12. On the other hand, when the operating unit 15 is not performing operations (i.e., when the sensor module 10 is in the second operating state), the sensor nodes 11 in the operating state send AE signals to the AFEs 14.

The sensor nodes 11 in the dormant state wait until the operating unit 15 receives a return signal. When the operating unit 15 receives a return signal, the power supply state of the sensor nodes 11 in the dormant state switches to the operating state.

Meanwhile, a series of AE signals attributed to a fracture developed in the PC cable continues for a period of about 30 seconds to one minute. In contrast, the period of time taken by the sensor nodes 11 in the dormant state to return to the operating state in response to a return signal is of the order of milliseconds. For that reason, even if the sensor nodes 11 return to the operating state after the fracture has developed, it is still possible to detect the AE signals.

After returning to the operating state from the dormant state, the concerned sensor nodes 11 again switch to the dormant state after the elapse of a period of time equal to or greater than a third threshold value. Herein, the third threshold value can be set in an arbitrary manner. For example, the third threshold value can be set in the range of 30 seconds to one minute.

When the sensor module 10 is in the first operating state, the comparing unit 12 receives AE signals from the sensor nodes 11. Then, the comparing unit 12 compares whether or not the magnitude of the AE signals is equal to or greater than a first threshold value. If the magnitude of the AE signals is equal to or greater than the first threshold value, the comparing unit 12 requests the communicating unit 13 to send a return signal so that the sensor modules 10 in the dormant state and the sensor nodes 11 in the dormant state return to the operating state.

The communicating unit 13 performs communication with other functional blocks and other devices. For example, in the first operating state of the sensor module 10, when the comparing unit 12 issues a request for sending a return signal, the communicating unit 13 sends a return signal to the corresponding operating unit 15 and to the communicating unit 13 of the other sensor modules 10 that are in the dormant state. In the dormant state of another sensor module 10, the communicating unit 13 receives the return signal and inputs it to the operating unit 15. Meanwhile, the communication method implemented in the communicating unit 13 can be either of the wired type or of the wireless type.

When the sensor module 10 is in the second operating state, the AFEs 14 receive AE signals from the sensor nodes 11. Then, the AFEs 14 perform signal conditioning with respect to the AE signals. Herein, the signal conditioning performed by the AFEs 14 includes, for example, amplification of the AE signals and removal of noise components from the AE signals. Subsequently, the AFEs 14 input the post-conditioning AE signals to the operating unit 15. In the following explanation according to the first embodiment, there is no essential difference between the post-signal-conditioning AE signals and the AE signals. Hence, for the sake of illustration, the signals outputs from the AFEs 14 are also simply referred to as AE signals.

The operating unit 15 performs computing operations. Herein, the operating unit 15 is, for example, a micro processing unit (MPU). For example, when the sensor module 10 is in the second operating state, the operating unit 15 receives AE signals from the AFEs 14. Then, the operating unit 15 performs predetermined operations with respect to the AE signals and sends, to a server device (described later) via the communicating unit 13, predetermined parameters or a warning based on the operation result.

Figure 6:
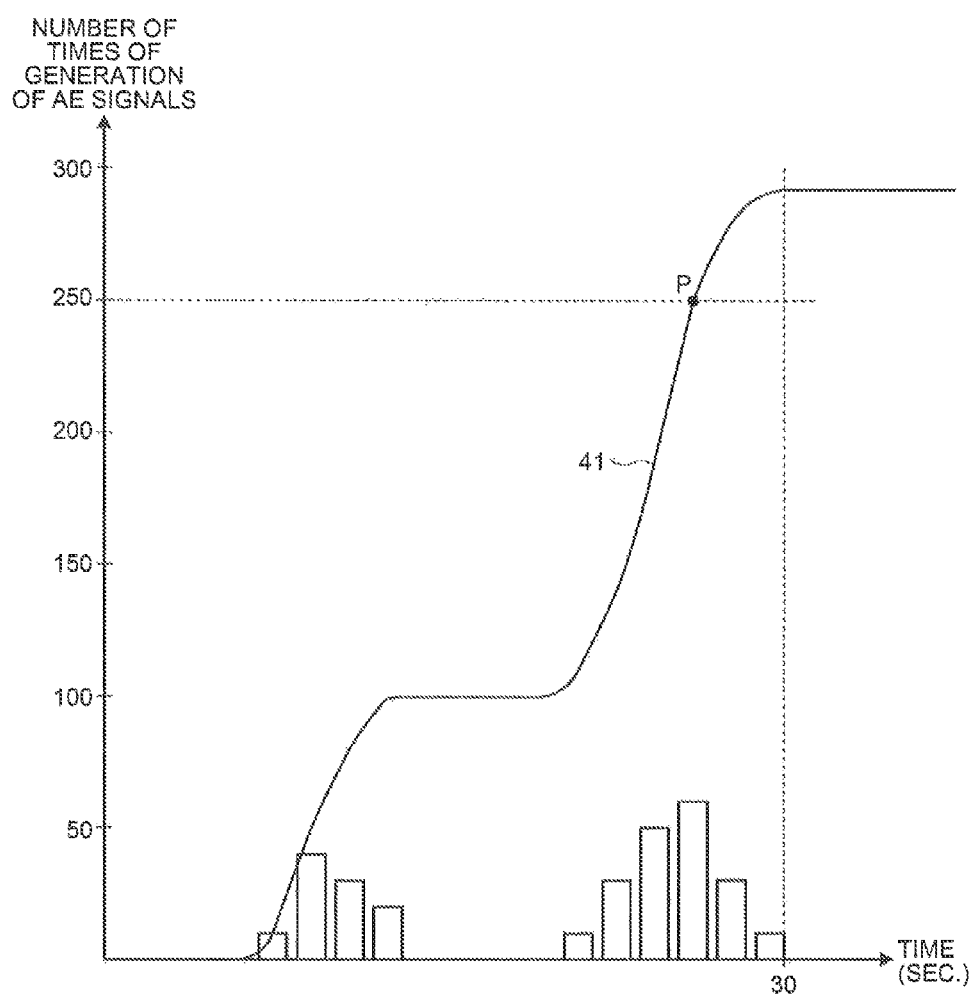
FIG. 6 is a diagram illustrating an example of predetermined operations according to the embodiment.

FIG. 6 is a diagram illustrating an example of the predetermined operations according to the embodiment. In FIG. 6 is illustrated an example in which the operating unit 15 counts the number of times of generation of AE signals and performs operations based on that count. Herein, the operating unit 15 counts the number of times of generation of AE signals (counts an AE count) according to, for example, the number of times for which the amplitude of the AE waveform exceeds a predetermined displacement. Moreover, the operating unit 15 determines whether or not the AE count during a predetermined period of time since the start of counting is equal to or greater than a fourth threshold value. In the example illustrated in FIG. 6, the fourth threshold value is set to 250. Moreover, the predetermined period of time is set, for example, in the range of 30 seconds to 60 seconds. If the AE count during the predetermined period of time since the start of counting is equal to or greater than the fourth threshold value, then the operating unit 15 determines whether or not a measurement transition curve 41, which represents the transition of the total number of times of generation of AE signals up to the fourth threshold value (the position of a point P), is similar to a fracture-time transition curve, which is created from the total number of times of generation of AE signals when a fracture develops in the PC cable as illustrated in FIG. 2. If the two curves are similar, then the operating unit 15 issues a warning to the server device (described later) via the communicating unit 13.

Meanwhile, the operations based on the number of times of generation are not limited to the operations described above. Alternatively, for example, without performing the determination using the fourth threshold value, the operating unit 15 may determine whether or not the measurement transition curve 41, which is based on the number of times of generation during a predetermined period of time, is similar to the fracture-time transition curve. Still alternatively, for example, instead of using the transition of the total number of times of generation of AE signals for similarity determination, the operating unit 15 can determine whether or not the transition of the number of times of generation of AE signals within a predetermined period of time is similar to the transition of the number of times of generation of AE signal when a fracture develops in the PC cable.

Meanwhile, the operations of the operating unit 15 are not limited to counting the number of times of generation of AE signals. Alternatively, for example, the operating unit 15 can perform the operation of extracting predetermined parameters from the AE waveform. Examples of the predetermined parameters include parameters indicating the frequency of AE signals, the energy of AE signals, and the duration of AE waves.

Returning to the explanation with reference to FIG. 5, when the detection system 1 is operational in the first operating state, the operating unit 15 decides on the sensor nodes 11 that are to be switched to the operating state. Regarding the method of deciding on the sensor nodes 11 that are to be switched to the operating state, the detailed explanation is given later.

Meanwhile, when a return signal is received, the operating unit 15 changes the power supply state of the sensor module 10 and the sensor nodes 11. For example, the operating unit 15 controls a switch on the power-supply line and changes the power supply state of the sensor module 10 and the sensor nodes 11.

The power supply 16 is connected to the sensor node 11, the comparing unit 12, the communicating unit 13, the AFEs 14, and the operating unit 15. For example, the power supply 16 is an energy harvesting module generating vibration-generated power and solar power, as well as a battery cell. Given below is the explanation about the power supply states in the cases in which the sensor module 10 is in the dormant state, the first operating state, and the second operating state.

<Case in which the Sensor Module 10 is in the Dormant State>

The power supply 16 supplies electrical power in such a way that the communicating unit 13, which receives return signals, is operational in the operating state. At that time, the power supply 16 supplies electrical power in such a way that the sensor nodes 11, the comparing unit 12, the AFEs 14, and the operating unit 15 are operational in the dormant state. When the operating unit 15 receives, via the communicating unit 13, a return signal from another sensor module 10; the power supply 16 supplies electrical power in such a way that the concerned sensor module 10 is operational in the second operating state.

<Case in which the Sensor Module 10 is in the First Operating State>

The power supply 16 supplies electrical power to the comparing unit 12, the communicating unit 13, and the sensor nodes 11 that are in the operating state and are connected to the power supply 16. At that time, the power supply 16 supplies electrical power in such a way that the AFEs 14, the operating unit 15, and the sensor nodes 11, which are in the dormant state and are connected to the power supply 16, are operational in the dormant state. However, alternatively, it is also possible that the power supply 16 does not supply electrical power to the AFEs 14, the operating unit 15, and the sensor nodes 11 that are not in the operating state but are connected to the power supply 16. As a result of setting the sensor module 10 in the first operating state, the detection system 1 can be operated over a long period of time. When the operating unit 15 receives a return signal, the power supply 16 supplies electrical power in such a way that the sensor module 10 is operational in the second operating state.

<Case in which the Sensor Module 10 is in the Second Operating State>

The power supply 16 supplies electrical power in such a way that the sensor node 11, the comparing unit 12, the communicating unit 13, the AFEs 14, and the operating unit 15 are operational in the operating state.

Given below is the explanation of an example of the transition of the power supply states of the detection system 1 according to the embodiment.

Figure 7:
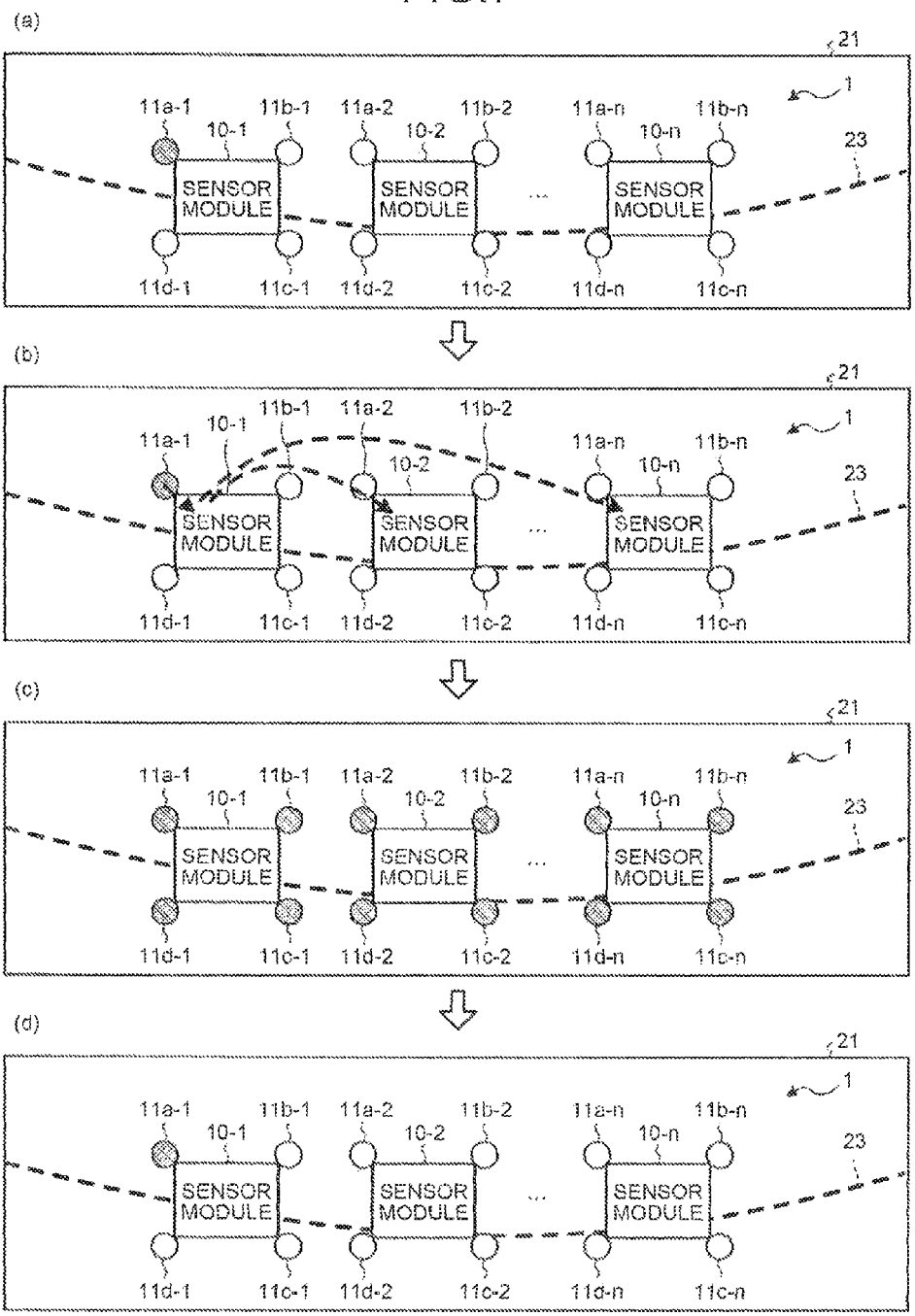
FIG. 7 is a diagram illustrating an example of the transition of the power supply states of the detection system according to the embodiment.

FIG. 7 is a diagram illustrating an example of the transition of the power supply states of the detection system 1 according to the embodiment.

In (a) in FIG. 7 is illustrated an example in which the detection system 1 is in the first operating state. Moreover, the sensor node 11a-1 is in the operating state, while the sensor nodes 11 other than the sensor node 11a-1 are in the dormant state. Furthermore, the sensor module 10-1 is in the first operating state, while the sensor modules 10 other than the sensor module 10-1 are in the dormant state.

In (b) in FIG. 7 is illustrated an example in which the sensor module 10-1 sends a return signal. If the AE signals received by the comparing unit 12 from the sensor node 11a-1 have the magnitude equal to or greater than the first threshold value, then the communicating unit 13 of the sensor module 10-1 sends a return signal to the operating unit 15 and to the communicating unit 13 of the other sensor modules 10 in the dormant state. Upon receiving the return signal, the communicating unit 13 of the other sensor modules 10 in the dormant state inputs the return signal to the corresponding operating unit 15. As a result, the power supply state of the detection system 1 changes from the first operating state to the second operating state.

In (c) in FIG. 7 is illustrated an example in which the detection system 1 is in the second operating state. Herein, all of the sensor nodes 11 are in the operating state. Moreover, all of the sensor modules 10 are in the second operating state.

In (d) in FIG. 7 is illustrated an example in which the detection system 1 switches from the second operating state to the first operating state. Thus, the example illustrated in (d) in FIG. 7 represents the case in which the detection system 1 switches back to the first operating state identical to the example illustrated in (a) in FIG. 7.

Given below is the explanation of an example of the transition of the power consumption of the detection system 1 corresponding to the transition of the power supply states illustrated in FIG. 7.

Figure 8:
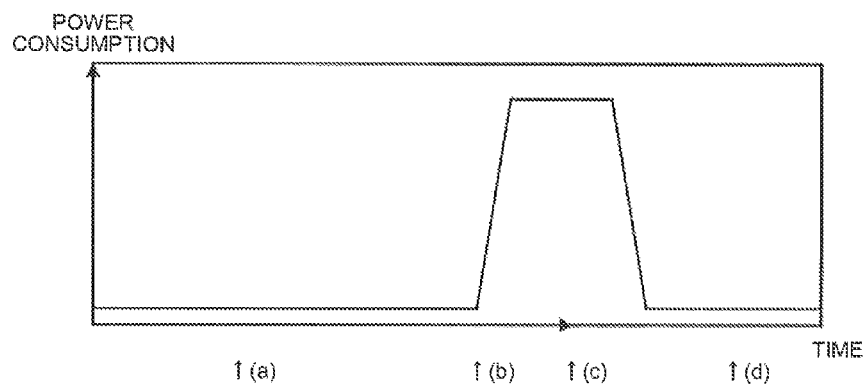
FIG. 8 is a diagram illustrating an example of the transition of the power consumption of the detection system according to the embodiment.

FIG. 8 is a diagram illustrating an example of the transition of the power consumption of the detection system 1 according to the embodiment. In FIG. 8, (a) corresponds to the case in which the power supply state of the detection system 1 is as illustrated in (a) in FIG. 7. That is, since the detection system 1 is in the first operating state, the power consumption becomes constant at a low level. In FIG. 8, (b) corresponds to the case in which the power supply state of the detection system 1 is as illustrated in (b) in FIG. 7. That is, when the sensor modules 10 in the dormant state and the sensor nodes 11 in the dormant state receive a return signal, the power supply state of the sensor modules 10 in the dormant state switches to the second operating state and the power supply state of the sensor nodes 11 in the dormant state switches to the operating state. For that reason, the power consumption of the detection system 1 increases in a gradual manner. In FIG. 8, (c) corresponds to the case in which the power supply state of the detection system 1 is as illustrated in (c) in FIG. 7. That is, since all of the sensor modules 10 are in the second operating state and since all of the sensor nodes 11 are in the operating state, the power consumption of the detection system 1 becomes constant at a high level. In FIG. 8, (d) corresponds to the case in which the power supply state of the detection system 1 is as illustrated in (d) in FIG. 7. That is, since the detection system 1 switches back to the first operating state identical to (a) in FIG. 7, the power consumption again becomes constant at a low level.

In (d) in FIG. 7, the explanation is given for the example in which the detection system 1 switches back to the first operating state identical to (a) in FIG. 7. However, alternatively, in the detection system 1, the source nodes 11 that are to be switched to the operating state can be changed.

Regarding the sensor nodes 11 in the operating state, even if those sensor nodes 11 are separated to some extent from the fracture position, as long as the sensor nodes 11 are within a range enabling detection of the AE signals at the moment at which a fracture develops, the sensor modules 10 that are connected to the sensor nodes 11 in the operating state can activate the sensor nodes 11 in the dormant state in a sufficiently quick manner. For example, inside the concrete or a steel structure, the elastic waves proceed at the speed of about 4000 m/s or more. Within a range of 50-meter radius from the fracture position, the fracture-time signals reach in about 13 milliseconds. Thus, from among the sensor nodes 11 arranged in an area that is wide to some extent, regardless of which sensor nodes 11 are selected as the sensor nodes 11 to be switched to the operating state, the fracture detection capability does not change in a large way.

Figure 9:
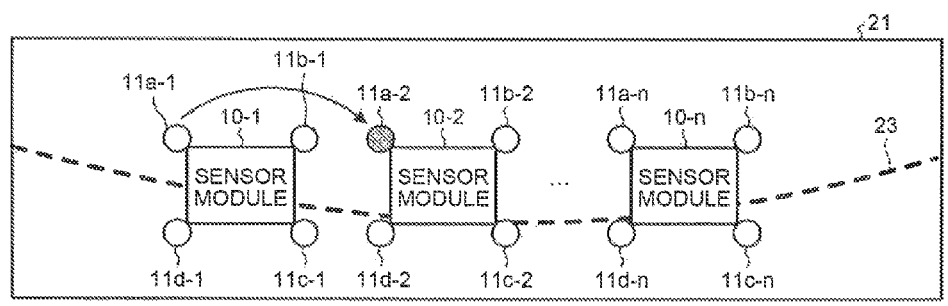
FIG. 9 is a diagram illustrating an example in which a sensor node in the operating state is changed according to the embodiment.

FIG. 9 is a diagram illustrating an example in which the sensor node 11 in the operating state is changed according to the embodiment. In FIG. 9 is illustrated an example in which the sensor node 11 in the operating state is changed from the sensor node 11a-1 to the sensor node 11a-2 by the operating unit 15. As a result, regarding the electrical power that is consumed, the source is changed from the power supply 16 of the sensor module 10-1 to the power supply 16 of the sensor module 10-2. Because of such operations, it becomes possible to prevent concentration of the load at a particular sensor module 10. Moreover, the consumption of battery cells can be spread across the power supplies 16. That makes it possible to lengthen the operating period of the detection system 1.

Given below is the explanation of an exemplary method by which the operating unit 15 decides on the sensor nodes 11 to be set in the operating state.

For example, assume that the operating unit 15 of the sensor module 10-1 is treated as the host sensor module. Then, in the case of switching the power supply state of the detection system 1 from the second operating state to the first operating state, the operating unit 15 of the sensor module 10-1 can decide on the sensor nodes 11 to be set in the operating state. In this case, information such as the priority and the operating period of all of the sensor nodes 11 in the detection system 1 is stored inside the operating unit 15 of the sensor module 10-1 or in a memory unit not illustrated in FIG. 5.

Given below is the explanation of a specific method for deciding on the sensor nodes 11 to be set in the operating state.

For example, based on the operating period of the sensor modules 10, the operating unit 15 can decide on the sensor nodes 11 to be set to the operating state when the detection system 1 is in the first operating state. More particularly, when the operating period of the sensor nodes 1 becomes equal to or greater than a second threshold value, the operating unit 15 changes the sensor nodes 11 to be set in the operating state. Herein, one second threshold value can be arbitrarily set based on the battery capacity of the power supply 16 of the sensor module 10.

Moreover, for example, every time the detection system 1 switches from the second operating state to the first operating state, the operating unit 15 can sequentially change, in round-robin fashion, the sensor nodes 11 to be set in the operating state. At that time, the operating unit 15 changes the sensor nodes 11 in the operating state to the sensor nodes 11 connected to other sensor modules 10. That enables achieving dispersion in the power consumption of the power supply 16 of each sensor module 10.

Meanwhile, the operating unit 15 need not always disperse the load evenly.

For example, when an energy harvesting module is mounted as the power supply 16, it is possible to think that the power generation amount varies depending on the installation location. In that case, the operating unit 15 can focus on the sensor nodes 11 that are connected to the sensor modules 10 generating a higher power generation amount and can decide on the sensor nodes 11 to be set in the operating state. As a result, the electrical power generated by each power supply 16 in the detection system 1 can be used in an effective manner.

Alternatively, for example, as the sensor nodes 11 to be set to the operating state, the operating unit 15 can decide on the sensor nodes 11 connected to the sensor modules 10 which are easy to maintain in regard to battery replacement or the like. As a result, the maintenance of the power supply 16, such as replacing the battery cells, becomes easier.

Given below is the explanation of a configuration of the server device according to the embodiment.

Figure 10:
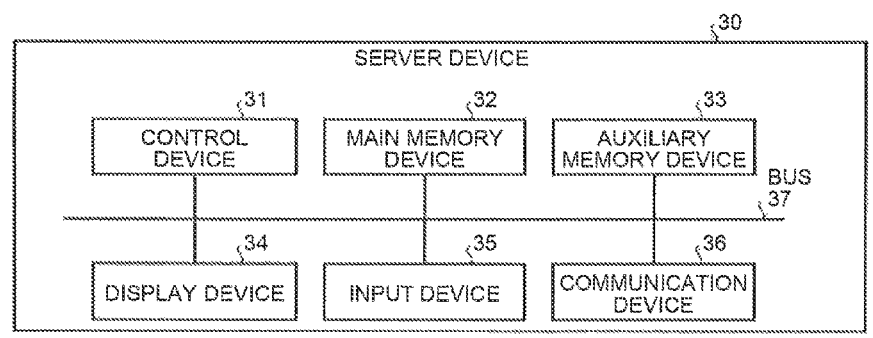
FIG. 10 is a diagram illustrating an exemplary configuration of a server device according to the embodiment.

FIG. 10 is a diagram illustrating an exemplary configuration of a server device 30 according to the embodiment.

The server device 30 according to the embodiment includes a control device 31, a main memory device 32, an auxiliary memory device 33, a display device 34, an input device 35, and a communication device 36. The control device 31, the main memory device 32, the auxiliary memory device 33, the display device 34, the input device 35, and the communication device 36 are connected to each other via a bus 37.

The control device 31 loads computer programs from the auxiliary memory device 33 into the main memory device 32, and executes them. The main memory device 32 is a memory such as a read only memory (ROM) or a random access memory (RAM). The auxiliary memory device 33 is a hard disk drive (HDD) or an optical drive.

The display device 34 is used to display information. For example, when the communication device 36 receives a warning from the detection system 1, information based on the warning is displayed on the display device 34. Herein, the display device 34 is, for example, a liquid crystal display. The input device 35 is an interface that enables operations of the server device 30. For example, the input device 35 is a keyboard or a mouse. The communication device 36 is an interface that enables communication with the detection system 1.

Meanwhile, all or some of the operations performed by the operating unit 15 of the sensor module 10 can be performed by the control device 31 of the server device 30. For example, the communication device 36 can receive the number of times of generation of AE signals from the communicating unit 13 of the sensor module 10, and the control device 31 can determine whether or not to display a warning on the display device 34.

Given below is the explanation of exemplary methods of operation of the detection system 1 according to the embodiment.

Figure 11:
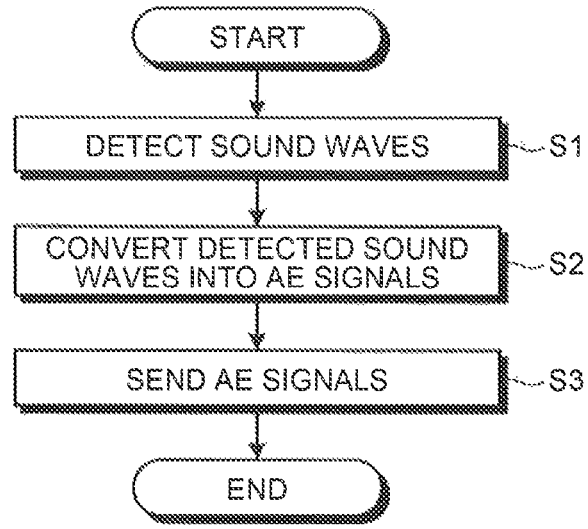
FIG. 11 is a flowchart for explaining an exemplary detection method according to the embodiment.

FIG. 11 is a flowchart for explaining an exemplary detection method according to the embodiment. Firstly, each sensor node 11 in the operating state detects the sound waves generated from the prestressed concrete 21 (Step S1). Then, the sensor node 11 in the operating state converts the sound waves into AE signals (detection signals) (Step S2). Subsequently, the sensor node 11 in the operating state sends the AE signals to the sensor module 10 (Step S3).

Figure 12:
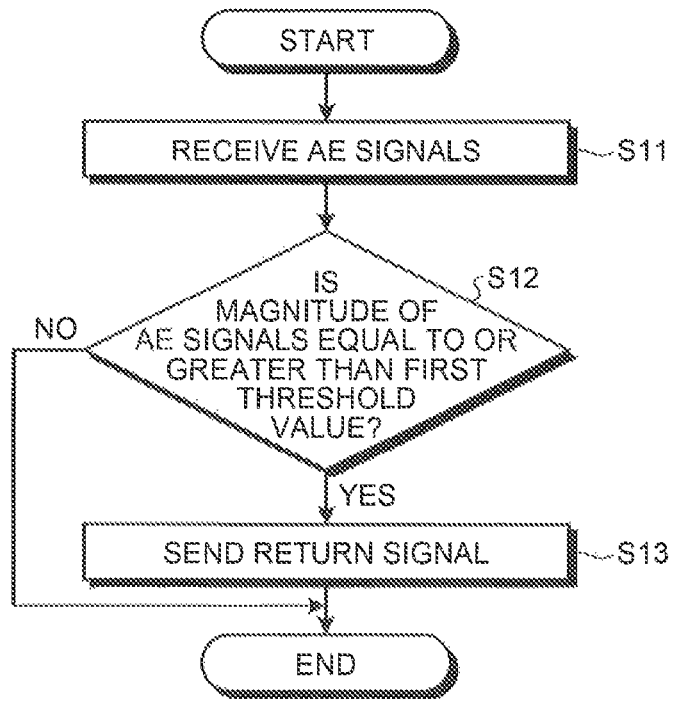
FIG. 12 is a flowchart for explaining an exemplary return determination method according to the embodiment.

FIG. 12 is a flowchart for explaining an exemplary return determination method according to the embodiment. Firstly, in the first operating state of each sensor module 10, the comparing unit 12 receives AE signals from the sensor nodes 11 (Step S11). Then, the comparing unit 12 compares whether or not the magnitude of the AE signals is equal to or greater than the first threshold value (Step S12). If the magnitude of the AE signals is equal to or greater than the first threshold value (Yes at Step S12), then the communicating unit 13 sends a return signal to the operating unit 15 and to the communicating unit 13 of the other sensor modules 10 in the dormant state (Step S13). However, if the magnitude of the AE signals is not equal to or greater than the first threshold value (No at Step S12), it marks the end of the operations.

Figure 13:
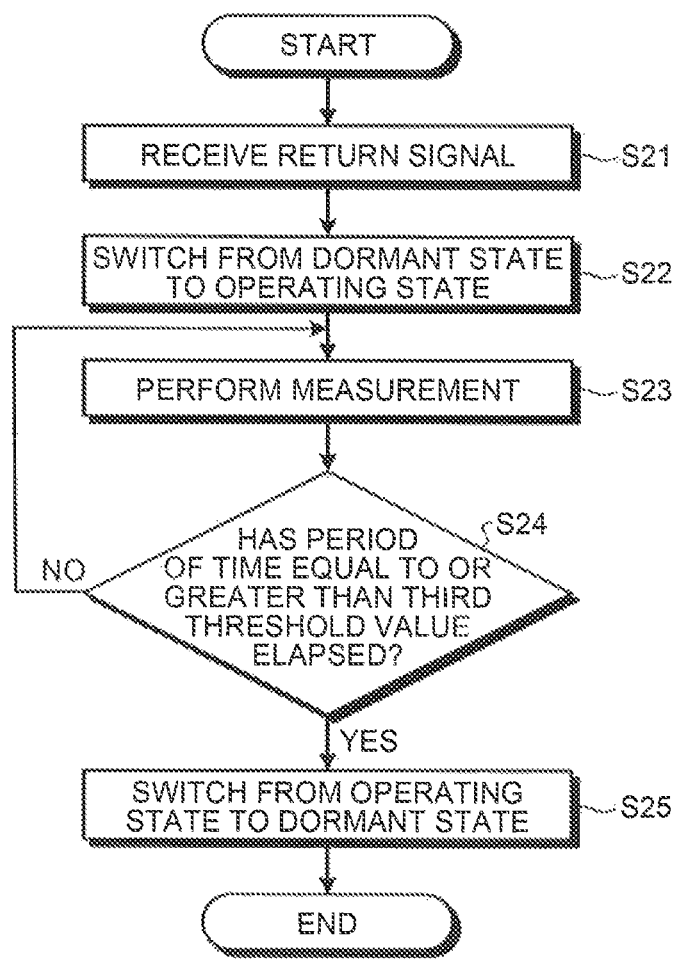
FIG. 13 is a flowchart for explaining a sequence of operations performed in each sensor node in the dormant state according to the embodiment.

FIG. 13 is a flowchart for explaining a sequence of operations performed in each sensor node 11 in the dormant state according to the embodiment. Firstly, in the sensor module 10 connected to the sensor node 11 in the dormant state, the operating unit 15 receives a return signal (Step S21). Then, the power supply stare of the sensor node 11 switches from the dormant state to the operating state (Step S22). The sensor node 11 in the operating state measures the prestressed concrete 21 (Step S23). More particularly, the sensor node 11 in the operating state detects the sound waves generated from the prestressed concrete 21 and converts the detected sound waves info AE signals (detection signals). Then, the sensor node 11 in the operating state determines whether or not a period of time equal to or greater than the third threshold value has elapsed since returning to the operating state (Step S24). If a period of time equal to or greater than the third threshold value has not elapsed since returning to the operating state (No at Step S24), the system control returns to Step S23. When a period of time equal to or greater than a third threshold value elapses since returning to the operating state (Yes at Step S24), the power supply state of the sensor node 11 switches from the operating state to the dormant state (Step S25).

Figure 14:
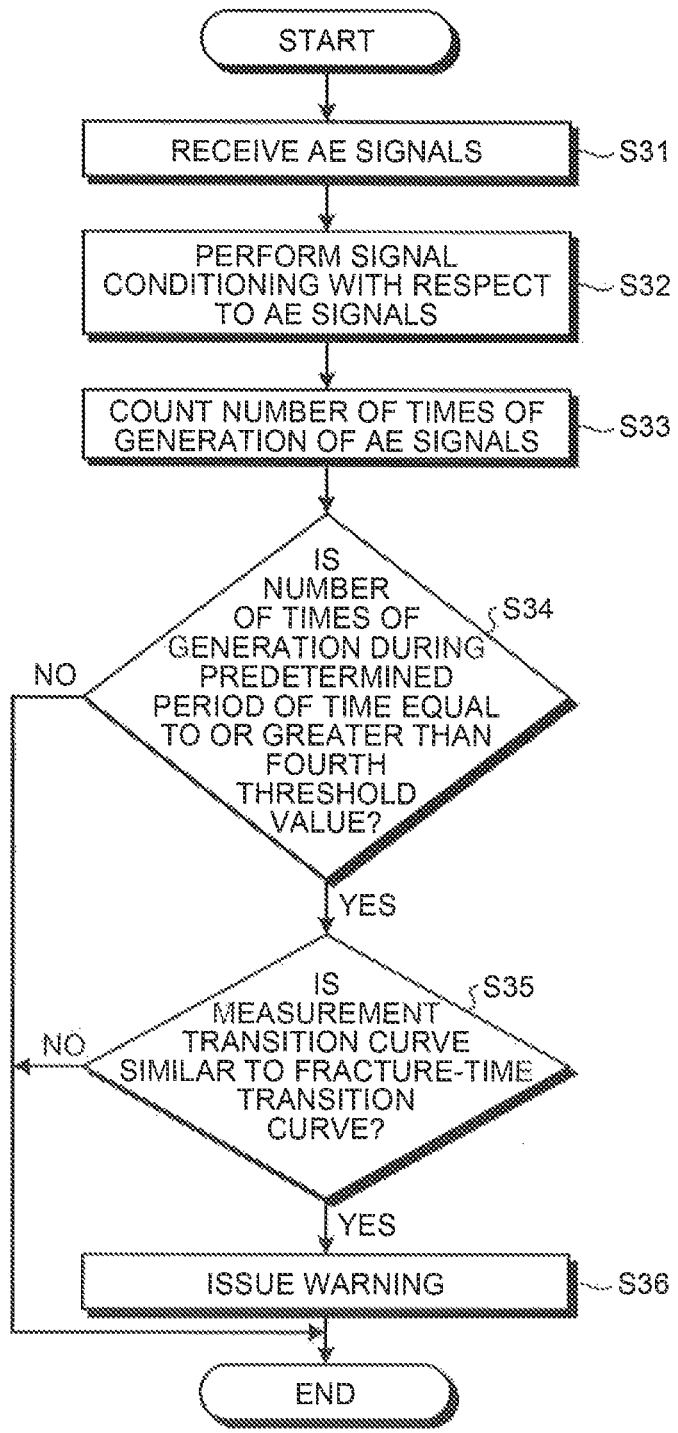
FIG. 14 is a flowchart for explaining an exemplary method of issuing a warning according to the embodiment.

FIG. 14 is a flowchart for explaining an exemplary method of issuing a warning according to the embodiment. Firstly, when in the second operating state of each sensor module 10, the AFEs 14 receive AE signals from the sensor nodes 11 (Step S31). Then, the AFEs 14 perform signal conditioning with respect to the AE signals (Step S32). Subsequently, the operating unit 15 counts the number of times of generation of AE signals (Step S33). Then, the operating unit 15 determines whether or not this e number of times of generation of AE signals during a predetermined period of time since the start of counting is equal to or greater than the fourth threshold value (Step S34).

If the number of times of generation of AE signals during a predetermined period of time since the start of counting is equal to or greater than the fourth threshold value (Yes at Step S34), then the operating unit 15 determines whether or not the measurement transition curve, which represents the transition of the total number of times of generation of AE signals up to the fourth threshold value, is similar to the fracture-time transition curve, which is created from the total number of times of generation of AE signals when a fracture develops in the PC cable (Step S35). If the two curves are similar (Yes at Step S35), the operating unit 15 issues a warning to the server device 30 (Step S36). However, if the two curves are not similar (No at Step S35), then it marks the end of the operations.

Meanwhile, if the number of times of generation of AE signals during a predetermined period of time since the start of counting is not equal to or greater than the fourth threshold value (No at Step S34), then it marks the end of the operations.

In the explanation of the flowchart illustrated in FIG. 14, at Step S34, the operating unit 15 determines whether or not the number of times of generation of AE signals is equal to or greater than the fourth threshold value. However, the operating unit 15 need not determine whether or not the number of times of generation of AE signals is equal to or greater than the fourth threshold value. Moreover, at Step S35, instead of using the transition of the total number of times of generation of AE signals for similarity determination, the operating unit 15 can determine whether or not the transition of the number of times of generation of AE signals within a predetermined period of time is similar to the transition of the number of times of generation of AE signal when a fracture develops in the PC cable.

Figure 15:
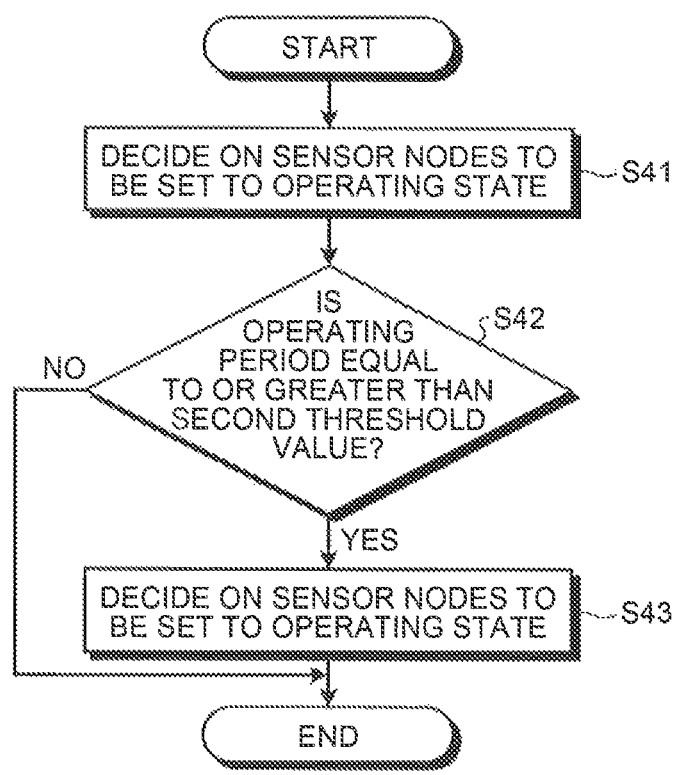
FIG. 15 is a flowchart for explaining an exemplary method of deciding the sensor nodes in the operating state according to the embodiment.

FIG. 15 is a flowchart for explaining an exemplary method of deciding the sensor nodes in the operating state according to the embodiment. Herein, the explanation is given for a case in which the operating unit 15 of the sensor module 10-1 is treated as a host sensor module and, when the power supply state of the detection system 1 switches from the second operating state to the first operating state, the operating unit 15 of the sensor module 10-1 decides on the sensor nodes 11 to be set in the operating state.

Firstly, when the power supply state of the detection system 1 switches from the second operating state to the first operating state, the operating unit 15 of the sensor module 10-1 decides on the sensor nodes 11 to be set to the operating state (Step S41). Then, at the time when the power supply state of the detection system 1 switches from the first operating state to the second operating state and again switches back to the first operating state, the operating unit 15 of the sensor module 10-1 determines whether or not the sensor nodes 11 that were switched to the operating state have the operating period equal to or greater than the second threshold value (Step S42). If the operating period is equal to or greater than the second threshold value (Yes at Step S42), the operating unit 15 refers to the information such as the priority and the operating period of the sensor nodes 11 and accordingly changes the sensor nodes 11 to be set to the operating state (Step S43). For example, as the sensor nodes 11 to be set to the operating state, the operating unit 15 decides on, for example, the sensor nodes 11 that have a short operating period and that have not been used much yet. Meanwhile, if the operating period is not equal to or greater than the second threshold value (No at Step S42), it marks the end of the operations.

As described above, the detection system 1 according to the embodiment includes the sensor modules 10, the sensor nodes 11 in the operating state, and the sensor nodes 11 in the dormant state in which the power consumption is held down as compared to the operating state. When the magnitude of the AE signals (detection signals) is equal to or greater than the first threshold value, each sensor module 10 switches the sensor nodes 11 in the dormant state to the operating state. As a result, after a fracture develops in the PC cable, when the PC cable refits in a stable state with the grout inside the sheath 23, a frictional sound generated between the PC cable and the grout can be detected. Hence, a fracture developed in the PC cable can be detected while holding down the power consumption of the detection system 1.

Meanwhile, the detection system according to the embodiment can be implemented for the purposes other than detecting a fracture developed in a PC cable. Moreover, under the condition of having a plurality of sensor nodes 11 installed, if detection of damage can be done without any problem regardless of the sensor nodes 11 set to the operating state, the detection system 1 according to the embodiment can be implemented in an identical manner.

For example, when a load gets applied to an arbitrary concrete structure that has deteriorated, the concrete structure generates AE waves. More the damage suffered by the concrete structure due to the load, greater is the number of AE waves generated by the concrete structure in the vicinity of the load. For that reason, in the wake of the detection of AE signals, which accompany the load, at arbitrary positions of the concrete structure by the sensor nodes 11 in the operating state, the other sensor nodes 11 in the dormant state are returned to the operating state and the condition of attenuation of the post-load AE signals is measured. With that, it is possible to detect the deteriorated positions. As a result, even when the detection system 1 according to the embodiment is implemented in an arbitrary concrete structure, the deteriorated positions can be identified while holding down the power consumption of the detection system 1.

Alternatively, for example, in the case in which damage suffered by a building structure is detected from the structural vibrations during an earthquake, in the wake of the detection of the P-waves, which are attributed to the earthquake, by the sensor nodes 11 in the operating state, the other sensor nodes 11 in the dormant state are returned to the operating state and the vibrations of the building structure due to the subsequent earthquakes can be measured. Herein, it is possible to think that, regardless of the locations in the building structure at which the sensor nodes 11 in the operating state are installed, the effect on the measurement result is not significant. Hence, even when the detection system 1 according to the embodiment is implemented in a building structure, the deteriorated positions can be identified while holding down the power consumption of the detection system 1.

While a certain embodiment has been described, the embodiment has been presented by way of example only, and is not intended to limit the scope of the inventions. Indeed, the novel embodiment described herein may be embodied in a variety of other forms; furthermore, various omissions, substitutions and changes in the form of the embodiment described herein may be made without departing from the spirit of the inventions. The accompanying claims and their equivalents are intended to cover such forms or modifications as would fall within the scope and spirit of the inventions.

What is claimed is:

1. A detection system comprising:
    a plurality of sensor nodes to detect sound waves generated from a prestressed concrete and convert the detected sound waves into detection signals; and
    a sensor module that is connected to the plurality of sensor nodes and receives the detection signals, wherein
    the plurality of sensor nodes includes at least a first sensor node and one or more other sensor nodes, wherein,
        the first sensor node is initially in an operating state; and
        the one or more other sensor nodes are initially in a dormant state in which power consumption is held down as compared to the operating state, and
    when a magnitude of the detection signals is equal to or greater than a first threshold value, the sensor module switches a second sensor node from among the one or more other sensor nodes from the dormant state to the operating state.

2. The system according to claim 1, wherein, when an operating period of the first sensor node in the operating state is equal to or greater than a second threshold value, the sensor module switches the first sensor node from the operating state to the dormant state and switches a sensor node from among the one or more other sensor nodes from the dormant state to the operating state.

3. The system according to claim 1, wherein, when a period of time equal to or greater than a third threshold value elapses since the second sensor node has been switched to the operating state by the sensor module, the second sensor node again returns to the dormant state.

4. The system according to claim 1, wherein
    the sensor module comprises:
        a comparing unit for determining whether or not the magnitude of the detection signals is equal to or greater than the first threshold value,
        an operating unit to perform a predetermined operation with respect to the detection signals, and
        a power supply that is capable of supplying electrical power to the plurality of sensor nodes, the comparing unit, and the operating unit, and
    when the magnitude of the detection signals is smaller than the first threshold value, the power supply supplies electrical power for operating the first sensor node in the operating state and for operating the comparing unit, and supplies electrical power lower than power consumption in the operating state to the one or more other sensor nodes in the dormant state and to the operating unit.

5. The system according to claim 1, wherein
    the dormant state represents a state in which power consumption is zero,
    the sensor module comprises:
        a comparing unit for determining whether or not magnitude of the detection signals is equal to or greater than the first threshold value,
        an operating unit to perform a predetermined operation with respect to the detection signals, and
        a power supply that is capable of supplying electrical power to the plurality of sensor nodes, the comparing unit, and the operating unit, and
    when the magnitude of the detection signals is smaller than the first threshold value, the power supply supplies electrical power for operating the first sensor node in the operating state and for operating the comparing unit, but does not supply electrical power to the one or more other sensor nodes in the dormant state and to the operating unit.

6. The system according to claim 1, wherein
    the sensor module is disposed in plurality, and each of a plurality of sensor modules is connected to one of the plurality of sensor nodes, and
    the detection system further comprises a communicating unit to send, when the magnitude of the detection signals is equal to or greater than the first threshold value, a return signal to the sensor modules to which the one or more other sensor nodes in the dormant state are connected, wherein the return signal enables switching of the second sensor node from the dormant state to the operating state.

7. The system according to claim 4, wherein
    the predetermined operation comprises:
        counting number of times of generation of the detection signals, and
        determining whether or not a measurement transition curve, which represents transition of the number of times of generation of the detection signals during a predetermined period of time since start of counting, is similar to a fracture-time transition curve, which represents transition of the number of times of generation of the detection signals when a fracture develops in a prestressed concrete (PC) cable, and
    the sensor module further comprises a communicating unit to issue a warning to a server device when the measurement transition curve, which represents transition of the number of times of generation of the detection signals during a predetermined period of time since start of counting, is similar to the fracture-time transition curve.

8. The system according to claim 5, wherein
    the predetermined operation comprises:
        counting number of times of generation of the detection signals, and determining whether or not a measurement transition curve, which represents transition of the number of times of generation of the detection signals during a predetermined period of time since start of counting, is similar to a fracture-time transition curve, which represents transition of the number of times of generation of the detection signals when a fracture develops in a prestressed concrete (PC) cable, and the sensor module further comprises a communicating unit to issue a warning to a server device when the measurement transition curve, which represents transition of the number of times of generation of the detection signals during a predetermined period of time since start of counting, is similar to the fracture-time transition curve.

9. The system according to claim 4, wherein the predetermined operation includes calculating a predetermined parameter from the detection signals, and the sensor module further comprises a communicating unit to send the predetermined parameter to a server device.

10. The system according to claim 5, wherein the predetermined operation includes calculating a predetermined parameter from the detection signals, and the sensor module further comprises a communicating unit to send the predetermined parameter to a server device.

11. A detection system comprising:

a plurality of sensor nodes to detect information and convert the detected information into detection signals; and a sensor module that is connected to the plurality of sensor nodes and that receives the detection signals, wherein the plurality of sensor nodes includes at least a first sensor node and one or more other sensor nodes, wherein, the first sensor node is initially in an operating state; and the one or more other sensor nodes are initially in a dormant state in which power consumption is held down as compared to the operating state, when a magnitude of the detection signals is equal to or greater than a first threshold value, the sensor module switches a second sensor node from among the one or more other sensor nodes from the dormant state to the operating state, and when an operating period of the first sensor node in the operating state is equal to or greater than a second threshold value, the sensor module switches the first sensor node in the operating state to the dormant state and switches the second sensor node from among the one or more other sensor nodes from the dormant state to the operating state.

12. A detection method implemented in a detection device that includes a plurality of sensor nodes including at least a first sensor node and one or more other sensor nodes, wherein the first sensor node is initially in an operating state and the one or more other sensor nodes are initially in a dormant state in which power consumption is held down as compared to the operating state, the detection method comprising:

detecting sound waves generated from a prestressed concrete and converting the detected sound waves into detection signals, by the first sensor node in the operating state;

receiving, by a sensor module that is connected to the plurality of sensor nodes, the detection signals from the first sensor node in the operating state; and switching, by the sensor module, a second sensor node from among the one or more other sensor nodes from the dormant state to the operating state when magnitude of the detection signals is equal to or greater than a first threshold value.

* * * * *